United States Patent [19]

Lo Duca

[11] Patent Number: 4,994,044
[45] Date of Patent: Feb. 19, 1991

[54] PROTECTED NEEDLE SYRINGE

[76] Inventor: Carmelo Lo Duca, Via Val di Sole, 11 - 20141, Milan, Italy

[21] Appl. No.: 420,319

[22] Filed: Oct. 12, 1989

[30] Foreign Application Priority Data

Oct. 18, 1988 [IT] Italy .................. 22345 A/88

[51] Int. Cl.⁵ .................. A61M 5/32; A61M 5/00
[52] U.S. Cl. ..................... 604/192; 604/110
[58] Field of Search ............... 604/192, 193, 110, 226, 604/243, 192

[56] References Cited

U.S. PATENT DOCUMENTS

| | | | |
|---|---|---|---|
| 2,728,341 | 12/1955 | Roehr | 604/193 |
| 2,828,743 | 4/1958 | Ashkenaz et al. | 604/243 |
| 3,107,785 | 10/1963 | Roehr | 604/194 |
| 3,320,954 | 5/1967 | Cowley | 604/110 |
| 3,534,734 | 10/1970 | Budreck | 604/226 |
| 3,903,886 | 9/1975 | Omotani | 604/193 |
| 4,027,669 | 6/1977 | Johnston et al. | 604/110 |
| 4,270,536 | 6/1981 | Lemelson | 604/226 |
| 4,281,653 | 8/1981 | Barta et al. | 604/192 |
| 4,303,069 | 12/1981 | Cohen | 604/201 |
| 4,717,386 | 1/1988 | Simmons | 604/192 |
| 4,735,617 | 4/1988 | Nelson et al. | 604/192 |
| 4,740,204 | 4/1988 | Masters et al. | 604/192 |
| 4,747,835 | 5/1988 | Sandhaus . | |
| 4,808,169 | 2/1989 | Haber et al. | 604/110 |
| 4,850,970 | 7/1989 | Sutherland | 604/192 |
| 4,863,433 | 9/1989 | Payne et al. | 604/194 |

FOREIGN PATENT DOCUMENTS

| | | | |
|---|---|---|---|
| 0047442 | 3/1982 | European Pat. Off. . | |
| 0360168 | 3/1962 | Switzerland | 604/193 |
| 0708707 | 5/1954 | United Kingdom | 604/192 |
| 2198353 | 6/1988 | United Kingdom . | |
| 2210270A | 6/1989 | United Kingdom . | |
| 8806463 | 9/1988 | World Int. Prop. O. | 604/243 |

Primary Examiner—C. Fred Rosenbaum
Assistant Examiner—Sharon Rose
Attorney, Agent, or Firm—Oblon, Spivak, McClelland, Maier & Neustadt

[57] ABSTRACT

Syringe for medical use of the disposable type provided with a hollow cap (40; 60; 60') that can be superimposed to the needle to protect it after carrying out the injection; the internal surface of the cap, close to its opening, and the external surface of the collar (44) for needle connection to the syringe have a substantially complementary shape. Close to the opening of the cap cavity, members 48, 61) are provided that firmly engage the collar (44) of the needle when it is forced into the cap cavity.

Preferably, the cap comprises a support base (70, 71) to keep it in an upright position with the opening of cavity upwards when said cap is removed from the needle (46) and is laid on a support plane.

9 Claims, 1 Drawing Sheet

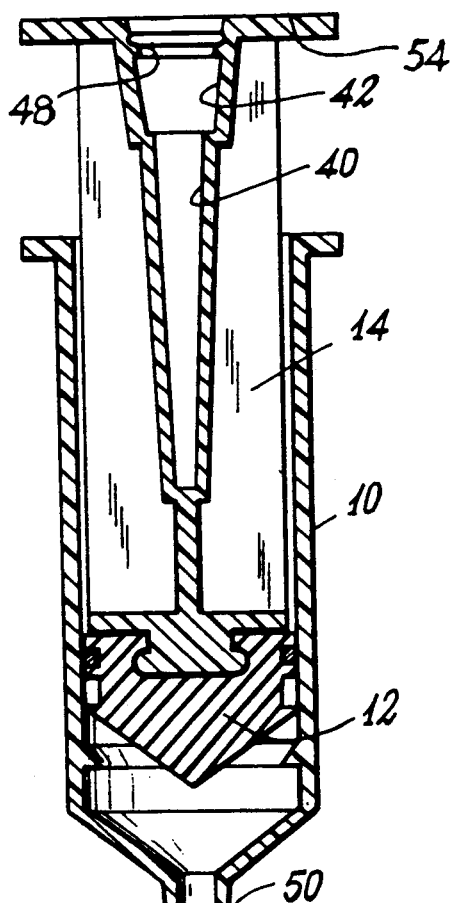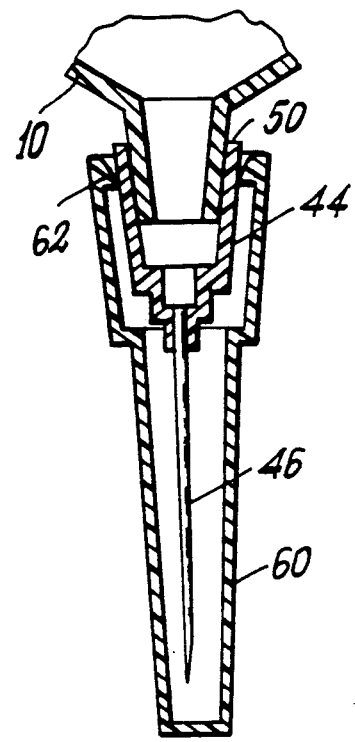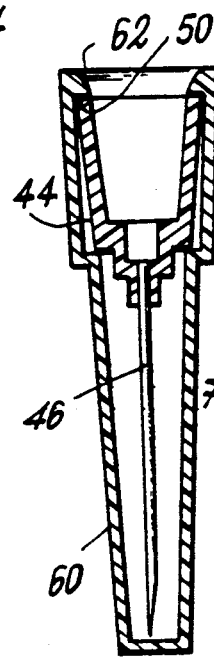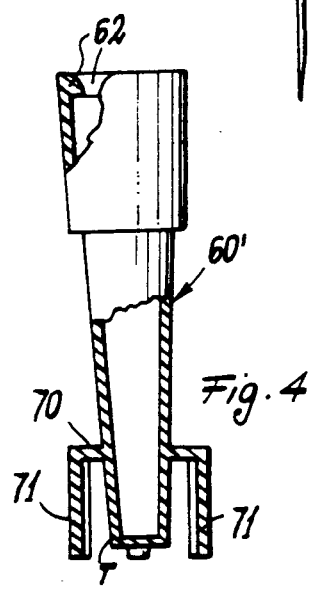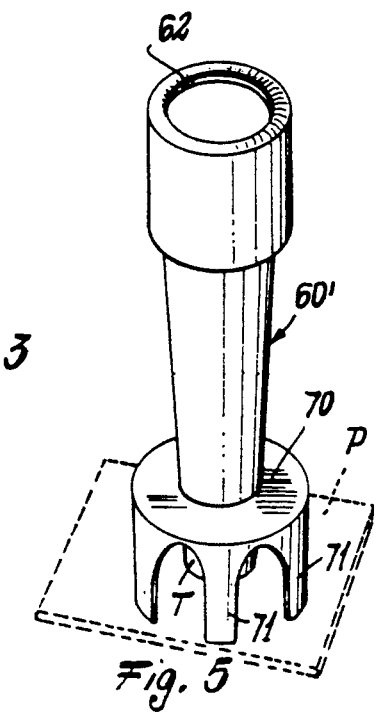

PROTECTED NEEDLE SYRINGE

BACKGROUND OF THE INVENTION

The present invention concerns a syringe for medical use, and more precisely a disposable syringe with protected needle.

It is known that the syringes of said type essentially comprise a hollow body, said body having a cylindrical shape with one end open, the other end being tapered and having such a shape as to receive a normal needle for injections. Within the cylindrical body a tight sealing piston can be moved in both directions, said pistons being driven by means of a stem that projects out of said open end of the cylindrical body.

At the moment of sale, the syringe needle is normally protected by means of a cap to be removed before using the syringe.

These syringes have the cylindrical body, stem and cap made of a substantially stiff synthetic material, the piston being on the contrary made of rubber or a resilient synthetic material having a suitable hardness. The syringe is employed in the following known way.

After removing the needle protection cap by grasping with the fingers the tip of the stem, the piston is shifted away from its position by the needle, or terminal position, in which the piston normally is at the moment the syringe is purchased. This displacement causes a depression to arise inside the syringe, by means of which, from a vial or ampoule, the proper amount of liquid drug is sucked through the needle.

Thereafter, the injection is performed in the usual known way. The needle protection cap is finally put on again before disposing of the whole assembly.

The low-cost syringes made of synthetic material are normally used only once, and then disposed off. This is due to obvious hygienic reasons that have become even more stringent, nowadays, mainly due to the diffusion of AIDS (acquired immuno-deficiency syndrome), one of the best transmission vehicles for which is indeed the used syringe.

It is however evident, that the protection cap can be easily removed, for example by children that might find said used syringes, or can be pulled-out accidentally during the transportation of waste into which the syringes are normally thrown with the serious troubles this can cause.

SUMMARY OF THE INVENTION

The present invention aims to eliminating the above-mentioned dangers by creating a syringe that, after it has been used, allows the risk of being accidentally stung for a person that imprudently or uncosciously touches said used syringes to be avoided.

Said aim is achieved by means of the syringe which, according to the invention, comprises a needly having, at its end opposite to its tip, a collar with a frustum of cone shaped outer surface, a cap being provided to protect the needle after use, said cap having a cavity in which the needle can be completely inserted and protected, said cavity being open at one of its ends where a seat that is substantially complementary to that of the needle collar is formed, characterized in that the cap, close to its open end, is provided with elastically deformable catching members, said members strongly engaging the collar of the needle when the needle is forced and completely pushed into the cap cavity.

The catching members provided on the internal surface of the cap can consist of a circular rib laying in a plane perpendicular to the axis of the cap. Said rib is preferably continuous, even though a rib divided in several lenghts might be acceptable as well. Said rib preferably has a saw-tooth shaped cross-section, the steeper side of the tooth being directed towards the closed cap end.

The catching member of the cap can simply consist of the outer top edge on the frustum of cone shaped needle collar or they may consist of a suitable groove or rib on the external side surface of said needle collar, said groove or rib having a surface that is adapted to engage the steep side of the saw-tooth shaped rib when one tries to remove the cap.

Preferably, the cap comprises a support base on which the cap can stand for the needle to be easily and safety introduced into the protection hollow of said cap.

BRIEF DESCRIPTION OF THE DRAWINGS

The invention will be better understood based on the following description of three embodiments thereof, which are merely illustrative examples. In the description, reference is made to the enclosed drawing in which: FIG. 1 is an axial-sectional view of a syringe of the disposable type showing a first embodiment of the invention;

FIG. 2 is an axial-sectional view of the lower end of a normal syringe with the needle-protection cap, before the syringe has been used, and shows a second embodimnt of the invention;

FIG. 3 is similar to FIG. 2 but relates to the situation after the syringe has been used, with the needle already safely protected again.

FIG. 4 and 5 show a partly sectional side elevation and a perspective views, respectively, of a different embodiment of the needle protection cap.

DETAILED DESCRIPTION OF THE PREFERRED EMBODIMENTS

In FIG. 1 there is shown a syringe of the type that can not be re-used due to the fact that stem 14 comes off the piston 12 if one tries to suck a drug solution for a second time, said piston remaining in the cylindrical body 10. It is characterized in that the stem 14 is provided with a cap-shaped open cavity 40 that opens at the free end of stem 14.

Said cavity 40 essentially has the shape of an elongated frustum of cone comprising a first part 42 that is adapted to receive the connection collar 44 of needle 46 mounted on body 10, whereby needle 46 can be housed and retained in the rest of the cavity. The first part 42 of the cap-like cavity exhibits, near its opening, a circular rib 48 having a saw-tooth-like cross-sectional shape, the steeper side of the saw-tooth being directed downward (in respect of the figure).

After the syringe has been used to perform an injection, it is sufficient to pull in the axial direction the stem 14 outward, thus removing it from piston 12. Said stem 14, that defines the cavity 40, will then be pushed over the needle 46 that is mounted on the lower end of the syringe, thereby pushing the stem 14 upwards until, with a slight deformation of the annular rib with saw-tooth shape 48, said deformation being allowed by the material it is made of, said rib 48 snaps beyond the upper edge 50 of needle collar 44.

If now one tries to remove the syringe from stem 14 (that works also as a protection cap for needle 46) the needle will also be removed and remains in any case trapped within the cavity 40 of the stem 14.

As a result, needle 46 remains protected, thus avoiding the possibility of accidental stings.

The presence of the cavity 40 formed in stem 14 also increases the safety against accidental stinging when needle 46 is inserted into the cavity 40, because, during said operation, the stem is grasped with the fingers of the hand at its other end, opposite to (and therefore removed from) the end where the cavity opens.

In the embodiment of FIGS. 2 and 3, the syringe as sold has a protection cap 60 covering needle 46. Said cap 60 having a body defining a cavity is internally provided, close to its opening, with an annular, saw-tooth shaped rib 62 the steeper side of which is directed downward.

At the moment of manufacturing the syringe, the machine that applies the cap 60 will exert thereon such an axial force as to force the cap into the position shown in FIG. 2. The force with which cap 60 is applied will however not be so strong as to make it difficult to remove the cap with the hands at the moment the syringe is to be used, without causing the needle to be removed from cylinder 10.

After the injection, it will be sufficient to apply again cap 60 onto needle 46, forcing it until rib 62, due to its resilient deformation, snaps beyond the upper edge 50 of the collar 44 of the needle 46 (see FIG. 3). IF now one tries to remove cap 60, also the needle 46, trapped and protected therein, will be removed.

That is, the rib is sufficiently rigid to prevent the needle from coming out of the cavity of the cap, as a result of the rib 62 engaging the collar 44.

In FIGS. 4 and 5, an embodiment 60' of the needle protection cap is shown, said needle protection cap being similar to that shown in FIGS. 2 and 3 and differing therefrom in that from the external surface of the cap, in an intermediate position thereof and especially near its closed end, an annular flange 70 projects from which appendixes or feet 71 protrude that are clearly visible in FIGS. 4 and 5 in which, for the sake of clearness, the same reference number of FIGS. 2 and 3 have been used to show like structural parts.

Cap 60', after it has been removed from needle 46 (to the purpose of allowing the syringe to be used) can be laid in a stable upright position onto a support plane P, a portion of which is shown in dashed lines for the sake of evidence in FIG. 5.

After finishing using the syringe with the needle, cap 60' is clearly visible on its support plane and needle 46 can be introduced into the seat of said cap without the need that it is held with the hands, as can be easily understood, thus avoiding the risk that the needle point may sting the operator's fingers.

It can also be noted that the operator can optionally grasp with his fingers the closed end T of cap 60', in which case flange 70 will act as a protecting shield for maintaining the operator's fingers spaced from the body of the cap so that they are protected from a needle which pierces the body of the cap during insertion of the needle into the cap.

It is evident that also a different assembly from that shown in the figures can be suited to keep cap 60' in an upright position on a support plane: for example, the same end base T of the cap can be made larger so as to become a firm support base, or three or more support feet 71 can protrude directly from the external surface of cap 60' towards its free end T.

I claim:

1. A syringe for medical use of the disposable type, comprising:
   a needle having, at an end thereof opposite to its a tip, a collar with a frustrum of cone shaped outer surface,
   a cap for protecting the needle after use, said cap having a body defining a cavity in which the needle can be completely inserted and protected, said cavity being open at one of its ends and having a seat that is substantially complementary to that the needle collar formed at said one of its ends,
   wherein the cap, close to said open end, is provided with elastically deformable catching members, said catching members comprising means for engaging the collar of the needle when the needle is completely inserted in the cap cavity, and being sufficiently rigid to prevent the needle from coming out of the cavity as a result of the catching members engaging the collar and wherein said cap has a support base on a closed end thereof opposite to said open end, said support base having a width sufficient to stably support said cap in an upright position on a substantially horizontal support surface.

2. A syringe according to claim 1, wherein said catching members of the cap comprise at least one resilient rib, said rib extending in a plane that a perpendicular to the axis of the cap, said rib comprising means for engaging an external annular edge of the collar of the needle.

3. A syringe according to one of claims 1 and 2, wherein the cap covers the needle prior to use 4. A syringe according to claim 3, the open end of the cap has a funnel-like shape and is coaxial with the cap.

5. A syringe according to claim 3 wherein said cap has a closed end, including a support base mounted to the cap adjacent the closed end for supporting said cap in an upright position on the base.

6. A syringe according to claim 5, wherein said base comprises a flange, said flange projecting from the cap and having at least three appendixes protruding towards the closed end of the cap.

7. A syringe according to claim 2, said cavity is formed in the stem of the syringe, the stem thus comprising the needle protection cap.

8. A syringe for medical use of the disposable type, comprising:
   a needle having at an end thereof opposite to its tip, a collar with a frustrum of cone shaped outer surface,
   a cap for protecting the needle after use, said cap having a cavity in which the needle can be completely inserted and protected, said cavity being open at one of its ends and having a seat that is substantially complementary to that of the needle collar formed at said one of its ends,
   wherein the cap, close to said open end, is provided with elastically deformable catching members, said catching members comprising means for engaging the collar of the needle when the needle is completely inserted in the cap cavity,
   wherein said cap has a closed end including a support base mounted to the cap adjacent the closed end for supporting the cap in an upright position on the base, said base including a flange projecting from the cap and having at least three appendixes protruding towards the close end of the cap.

9. A syringe for medical use of the disposable type, comprising:

a needle having, at an end thereof opposite to its tip, a collar with a frustum of cone shaped outer surface, a cap for protecting the needle after use, said cap having a body defining a cavity in which the needle can be completely inserted and protected, said cavity being open at one of its ends and having a seat that is substantially complementary to that of the needle collar formed at said one of its ends, wherein the cap, close to said open end, is provided with elastically deformable catching members, said catching members comprising means for engaging the collar of the needle when the needle is completely inserted in the cap cavity, and being sufficiently rigid to prevent the needle from coming out of the cavity as a result of the catching members engaging the collar, and wherein said cap has, adjacent a closed end opposite said open end, shield means for maintaining a user's fingers spaced from the body of the cap, whereby a user's fingers are protected from a needle which pierces the body of the cap during the insertion of the needle into the cap.

* * * * *